(12) United States Patent
Connell et al.

(10) Patent No.: US 11,921,064 B2
(45) Date of Patent: Mar. 5, 2024

(54) DETECTOR ARRANGEMENT, DETECTION SYSTEM AND METHOD OF PROCESSING DATA FROM A DETECTOR ARRANGEMENT FOR HIGH THROUGHPUT DATA HANDLING

(71) Applicant: University of Johannesburg, Johannesburg (CA)

(72) Inventors: Simon Henry Connell, Johannesburg (CA); Martin Nkululeko Hogan Cook, Johannesburg (CA); Richard Charles Andrew, Johannesburg (CA)

(73) Assignee: University of Johannesburg, Johannesburg (ZA)

( * ) Notice: Subject to any disclaimer, the term of this patent is extended or adjusted under 35 U.S.C. 154(b) by 439 days.

(21) Appl. No.: 17/413,433

(22) PCT Filed: Dec. 11, 2019

(86) PCT No.: PCT/IB2019/060656
§ 371 (c)(1),
(2) Date: Jun. 11, 2021

(87) PCT Pub. No.: WO2020/121214
PCT Pub. Date: Jun. 18, 2020

(65) Prior Publication Data
US 2022/0057344 A1    Feb. 24, 2022

(30) Foreign Application Priority Data

Dec. 11, 2018  (ZA) .................................. 2018/08343

(51) Int. Cl.
*G01N 23/22* (2018.01)
*G01N 23/221* (2006.01)
(Continued)

(52) U.S. Cl.
CPC .......... *G01N 23/221* (2013.01); *G01N 33/381* (2013.01); *G01T 1/2985* (2013.01); *G01N 23/12* (2013.01)

(58) Field of Classification Search
CPC .... G01N 23/12; G01N 23/221; G01N 33/381; G01T 1/2985
See application file for complete search history.

(56) References Cited

U.S. PATENT DOCUMENTS

2018/0136340 A1* 5/2018 Nelson ................... G01T 1/1611
2018/0136344 A1* 5/2018 Nelson ................... A61B 6/4417
2018/0172849 A1* 6/2018 Nelson ................... G01T 1/20182

FOREIGN PATENT DOCUMENTS

CA        2360656 A1    4/2002
WO    WO-2005/088283 A1    9/2005

OTHER PUBLICATIONS

Ballestrero et al., "Mineral-PET: Kimberlite sorting by nuclear-medical technology," <https://www.researchgate.net/publication/228549696_Mineral-PET_Kimberlite_sorting_by_nuclear-medical_technology>, retrieved on Mar. 16, 2022 (2010) (15 pages).
(Continued)

*Primary Examiner* — Mark R Gaworecki
(74) *Attorney, Agent, or Firm* — Clark & Elbing LLP

(57) ABSTRACT

The invention relates to a detection arrangement, a detection system comprising said arrangement, and a method of processing data from said arrangement. The detector arrangement disclosed comprises at least one array of detectors, wherein the detectors are configured to detect photons emitted from an object as a result of positron annihilation due to irradiation of the object with photons of a predetermined energy. Each detector in the array is linked to or associated with one or more other detector in the array to define a region of interest (RoI). The detector arrangement comprises or is communicatively coupled to a coincidence
(Continued)

trigger unit which is configured to register or determine a coincidence in response to receiving detection signals from two different detectors forming part of the same RoI and indicating detection of substantially back-to-back co-linear and co-incident photons in the RoI.

20 Claims, 7 Drawing Sheets

(51) Int. Cl.
    *G01N 33/38*     (2006.01)
    *G01T 1/29*     (2006.01)
    *G01N 23/12*     (2018.01)

(56) References Cited

OTHER PUBLICATIONS

International Search Report and Written Opinion for International Application No. PCT/IB2019/060656, dated May 26, 2020 (11 pages).

\* cited by examiner

DETECTOR ARRANGEMENT, DETECTION SYSTEM AND METHOD OF PROCESSING DATA FROM A DETECTOR ARRANGEMENT FOR HIGH THROUGHPUT DATA HANDLING

FIELD OF THE INVENTION

This invention relates, generally, to the detection of particles or substances of interest in objects. More specifically, the invention relates to a detection arrangement and to a detection system. The invention also relates to a method of processing data from a detector arrangement.

BACKGROUND OF THE INVENTION

In conventional diamond mining operations, vast amounts of resources such as water and energy are required to process mostly barren rock in order to recover diamonds. Processing of the rock typically includes a damaging sequence of rock crushing and diamond recovery, often with a relatively low yield, for example, approximately 1 carat per ton of rock processed. However, crushing of rock in a conventional fashion may lead to diamond breakage, thereby reducing the profitability of a diamond mine.

Sensor- or detector-based technologies attempt to negate these undesirable effects by enabling early detection of relatively unprocessed diamond bearing rocks which can then be isolated and processed in an environmentally friendly manner that preserves diamond integrity. However, such technology produces data which must be processed in complex ways to enhance the sensitivity and accuracy of the diamond detection. This processing may make use of relatively complex algorithmic processes to achieve desired sensitivity at the cost of computational resources.

One prior art technology makes use of Positron Emission Tomography (PET) to be able to detect diamonds in rocks. This approach involves irradiating a rock with a gamma ray beam from bremsstrahlung of, for example, 40 MeV electrons, or a different source of photons other than bremsstrahlung, for example, inverse Compton scattering, or other techniques. The rock returns to moderate levels of specific activity within minutes, by which time the PET isotopes represent the dominant residual activity. When the $^{11}C$ pet isotope is the dominant activity, after about 30 minutes, the rock is then inspected by way of a detector arrangement to determine whether or not there is a diamond present therein.

Classification data generated when using this approach is usually associated with photons detected by the detector arrangement. These photons are emitted from the rock as a result of positron annihilation in the rock. When a PET isotope in the rock releases a positron particle through beta-decay, the positron annihilates with a nearby electron after following a short path that can involve multiple scattering events.

The most common outcome of this annihilation is the production of nearly co-linear back-to-back 511 keV gamma ray photons. Each photon then travels through the surrounding material, sometimes changing energy and direction along the way. When the photons reach the detector arrangement, the detector arrangement may output classification data in the form of detector strike/hit event data.

Known detection schemes range from simple detectors to relatively complex detector arrangements which typically include arrays of individual detectors. The simpler detectors may lack the required sensitivity unless they are only required to detect relatively large diamonds. It is therefore usually necessary to make use of more complex detector arrangements. However, a problem associated with the more complex prior art detector arrangements and the detection or classification systems to which they are coupled is that they may be unable to transmit and/or process data at the volumes and rates required.

The data transmitted and/or processed when inspecting irradiated rocks at a high throughput with sensitivity which is acceptable and commercially viable in a mining environment, where high volumes (e.g. approximately 700 tons of rock) are processed per hour, may exceed the transport capacity of a single high bandwidth link or the processing capacity of a single computer. This issue may be amplified by the fact that detection must typically be completed within seconds for downstream ejection systems to function effectively.

There are a number of reasons why it may be desirable to make provision for higher data rates. Examples are set out below.

As alluded to above, it may be desirable to find relatively small diamonds. A diamond can be said to be detected if enough information is gathered so that the detected diamond is statistically significant above random fluctuations in the background. In order to find smaller diamonds, it may be necessary to collect more data. This may be done by increasing the activation level of the irradiated rock and/or increasing detector coverage, both of which may lead to increased data rates.

It may also be desirable to search for, and find, diamonds in relatively large objects, such as relatively large kimberlite particles. The 511 keV photons detected in a PET detection method may be absorbed as they pass through kimberlite. Usually, two back-to-back photons must be detected at the same time in opposite planes of the detector arrangement (e.g. above and below the kimberlite) to form a line of response (LoR). The longer the path length through kimberlite, the greater the probability that a photon is absorbed, and that the LoR is not registered. As kimberlite particles increase in size (or as bed depth of kimberlite is increased), path length increases. This must be compensated for by increasing activation and therefore data rate.

Furthermore, it may be desirable to increase system throughput, e.g. the number of tonnes per hour that can be processed. To achieve this, it may be necessary to increase activation so that data is collected quickly, and material can move through detectors at a faster velocity. Throughput may also be increased by pushing a greater volume of activated rock through a detector arrangement at any given time. These techniques may increase data requirements of a detection system.

In addition, so-called "false positives" reduce the signal to noise ratio, making identification of diamonds harder. Moreover, "false positives" may unnecessarily increase data rates and may thus make it more difficult for a detection system to transmit and process data at satisfactory rates. LoRs are registered by locating two photons that arrive in opposite detector planes within a short time window, known as the "coincidence window" or "coincidence resolving time". This window defines the maximum time separation between coincident events are detected for a given detection system. If the difference in detection time of two events is less than the coincidence window, they are classified as coincident. The choice of coincidence window is an optimisation problem that depends on the system characteristics (degree of activation, volume of rock, detector size and shape, etc.). If the window is too short, good LoRs are lost; too long, and false positive LoRs are picked up.

Factors influencing the coincidence window include the flight time of the photons (if positron annihilation occurs closer to a top detector than a bottom one, for example, then the top photon arrives slightly earlier than the bottom photon due to the finite speed of light), properties of the detector arrangement and/or individual detectors (e.g. different scintillation crystals, which convert photons to light flashes, have different light pulse rise times and light yields) and electronics properties.

The non-zero length/time associated with coincidence windows implies that, during operation, a non-correlated random signal could arrive within the coincidence window of an event, which will lead to the creation of a "false" LoR, i.e. a LoR that consists of two detection events that are not the paired 511 keV photons arising from the same positron annihilation. For a given coincidence window size, the rate of false LoRs would typically increase as the roughly the square of the overall data rate increases, as there are more events per second, which increases the probability that one randomly arrives during the coincidence window. As the activation of rock increases, the number of false LoRs may increase dramatically.

It is therefore desirable to design a detection system which keeps the number of false LoRs down to a relatively small fraction of true LoRs. Activity should be sufficiently low considering the coincidence window leading to a tolerable false coincident rate, while the amount of LoRs that can be acquired for a given rock volume should be sufficiently high to be able to achieve the minimum detection required for the detection system to function at a satisfactory level.

There is a need for an arrangement, system and/or method capable of addressing or alleviating at least some of the aforementioned issues.

In the context of this specification, the term "object" may be understood to mean a rock particle such as kimberlite, irrespective of the size thereof, or a loose diamond. Thus the terms "object", "rock", "particle" and "kimberlite" may be used interchangeably herein. The term "object" may also extend to other objects which are imaged or analysed in a detection method, e.g. a human or animal body or body part of a body as the concepts contained herein apply mutatis mutandis to medical applications of PET.

SUMMARY OF THE INVENTION

In accordance with one aspect of the invention, there is provided a detector arrangement comprising at least one array of detectors, wherein the detectors are configured to detect photons emitted from an object as a result of positron annihilation due to irradiation of the object with photons of a predetermined energy, wherein each detector in the array is linked to or associated with one or more other detector in the array to define a region of interest (RoI), each RoI including a subset of the detectors in the array, and wherein the detector arrangement includes or is communicatively coupled to a coincidence trigger unit which is configured to register or determine a coincidence in response to receiving detection signals from two different detectors forming part of the same RoI and indicating detection of substantially back-to-back co-linear and co-incident photons in the RoI.

The detection of the substantially back-to-back co-linear and co-incident photons in the RoI may be used in the determination of material/s of interest in the object.

The predetermined energy may be energy at which giant dipole resonance (GDR) occurs due to a nuclear reaction between the photons and carbon, thereby enabling the detector arrangement to be used for the detection of diamond or other materials of interest. The photons may be gamma ray photons. The detector arrangement may be configured to detect photons having an energy level of approximately 511 keV and rejecting photons not having the energy level of approximately 511 keV.

As mentioned above, the object being imaged may not be limited to the mining context, but it could be biological material, or it could also be any other material or context. What is important is the need in PET either medical or not for high throughput PET data handling or processing. For example it could be the case for whole body PET or PET video, where rates and volumes of data are high.

The at least one array of detectors may include a pair of spaced apart detector arrays oriented generally parallel to each other. Each RoI may include at least one detector from each detector array and the coincidence trigger unit may be configured to register a coincidence in response to receiving detection signals from a detector from each detector array, provided the detectors are in the same RoI. In some embodiments, each RoI includes one detector from one of the arrays and a plurality of detectors from the other one of the arrays.

The coincidence trigger unit may be configured, in response to registering a coincidence, to transmit a coincidence signal back to each of the two detectors as trigger information indicative thereof. The detectors may be configured to transmit or publish event data relating to the registered coincidence signal to a specific data acquisition (DAQ) computer in response to receiving trigger information indicative of a coincidence signal. The trigger information may be the coincidence signal. In other example embodiments, there may also be a fast supervisory system(s) in hardware/firmware/software at the detector level that can establish the geometric information of both local sub-detector partners in a coincidence trigger event, further enabling the local detector unit to address its transmission to the correct data acquisition (DAQ) computer.

In accordance with another aspect of the invention, there is provided a detection system which includes a detector arrangement, a coincidence trigger unit and at least one DAQ computer substantially as described above.

In some embodiments, the system may include a plurality of DAQ computers. Each DAQ computer may be configured to receive event data only from detectors which form part of one or more RoIs which are associated with the particular DAQ computer.

The event data may be raw output data and each DAQ computer may be configured to determine a line of response (LoR) based on the raw output data received from the detectors. The LoR may correspond to an imaginary line through the object connecting strikes on detectors on opposite sides of the object, with the strikes corresponding to the back-to-back co-linear and co-incident photons emitted by or from the object.

In some embodiments, the detector arrangement may be configured to perform detection on a stream of objects passing through the detector arrangement, e.g. rock moving through/past the detector arrangement on a belt or other conveying arrangement.

It will be understood that the detectors as described herein may encircle the belt. In one example embodiment, the detectors may encircle the belt such that the LoR has an axis which is substantially transverse to a direction of transport of the object/s. In the case of medical applications, the detectors may encircle a patient and/or animal, or part thereof to achieve the same end as described herein.

The detection system may be configured to divide the stream of objects into virtual containers. Each LoR may be associated with at least one virtual container. Each DAQ computer may be configured to transmit LoRs to a volume processing computer or subsystem configured to process only LoRs relating to one or more particular virtual container. The volume processing computer or subsystem may be configured to form a PET image based on LoRs associated with a particular virtual container.

It will be appreciated that virtual containers may be fixed to belt-moving coordinates. In one example embodiment, the DAQ computer may be fixed to detector coordinates. In this regard, DAQ computers may not be fixed to virtual containers but process a continuous procession of virtual containers.

The detection system may include a plurality of processing nodes associated with each virtual container and/or each volume processing computer or subsystem, such that each processing node operatively handles a sub-volume of a volume associated with each virtual container.

Broadly, in accordance with another aspect of the invention, there is provided a method of processing data from a detector arrangement, wherein the detector arrangement includes at least one array of detectors, the method comprising:
    linking or associating each detector in the array with one or more other detector in the array to define a region of interest (RoI), each RoI including a subset of the detectors in the array;
    detecting, by the array of detectors, photons emitted from an object as a result of positron annihilation due to irradiation of the object with photons of a predetermined energy;
    receiving, by a coincidence trigger unit, detection signals from at least two of the detectors; and
    registering or determining a coincidence if the coincidence trigger unit receives detection signals from two different detectors forming part of the same RoI and indicating detection of substantially back-to-back co-linear and co-incident photons in the RoI.

The RoIs may overlap, so the subsets of detectors that form RoIs are not mutually exclusive subsets.

The method may further comprise:
    transmitting, by the coincidence trigger unit, trigger information indicative of a coincidence signal to each of the two detectors in response to registering or determining the coincidence; and
    transmitting or publishing, by the two detectors, event data relating to the registered coincidence to a data acquisition (DAQ) computer.

The detector system may include the capacity to reveal RoI information pertain to each LoR endpoint. The detector unit that has been triggered as having detected at least one of two coincident LoR endpoints, publishes this endpoint information to one or more separate systems at the next (DAQ) level. It will publish to more than one DAQ level system if there is ambiguity as to which detector RoI could have received the partner endpoint of the LoR. The geometrical part of the criteria for the validity of the LoR will then be determined at the DAQ level, and the LoR can be correctly formed. Also at this stage the assignment of the LoR to a virtual basket of moving rock can be established, for correct onward transmission. The detectors have intelligence that publishes their data to a different topologically independent network of DAQ computers, thereby achieving the separation of the signals over different networks.

In accordance with a further aspect of the invention, there is provided a diamond mine processing system which includes a detection arrangement and/or a detection system substantially as described above.

In yet a further aspect of the invention, there is provided a medical positron emission tomography (PET) system which comprises at least one of a detection arrangement substantially as described above, and a detection system substantially as described above.

It will be understood by those skilled in the art that the comments which are provided above with respect to each aspect of the invention may be applied mutatis mutandis to all aspects of the invention.

DETAILED DESCRIPTION WITH REFERENCE TO THE DRAWINGS

The following description of the invention is provided as an enabling teaching of the invention. Those skilled in the relevant art will recognise that many changes can be made to the embodiments described, while still attaining the beneficial results of the present invention. It will also be apparent that some of the desired benefits of the present invention can be attained by selecting some of the features of the present invention without utilising other features.

Accordingly, those skilled in the art will recognise that modifications and adaptations to the present invention are possible, and may even be desirable in certain circumstances, and are a part of the present invention. Thus, the following description is provided as illustrative of the principles of the present invention and not a limitation thereof.

It will be appreciated that the phrase "for example," "such as", and variants thereof describe non-limiting embodiments of the presently disclosed subject matter. Reference in the specification to "one example embodiment", "another example embodiment", "some example embodiment", or variants thereof means that a particular feature, structure or characteristic described in connection with the embodiment(s) is included in at least one embodiment of the presently disclosed subject matter. Thus, the use of the phrase "one example embodiment", "another example embodiment", "some example embodiment", or variants thereof does not necessarily refer to the same embodiment(s).

Unless otherwise stated, some features of the subject matter described herein, which are, described in the context of separate embodiments for purposes of clarity, may also be provided in combination in a single embodiment. Similarly, various features of the subject matter disclosed herein which are described in the context of a single embodiment may also be provided separately or in any suitable sub-combination.

Figure 1:
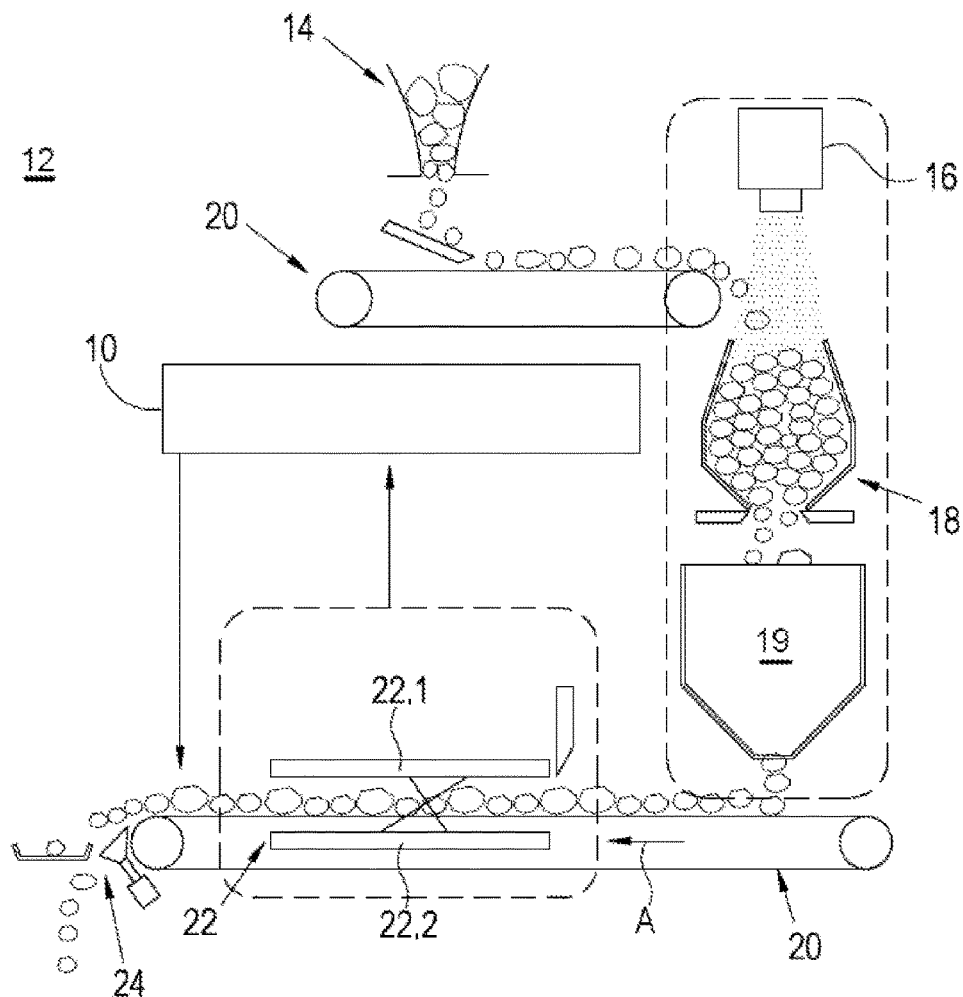
FIG. 1 shows a schematic diagram of an example of a diamond mine processing system in which embodiments of the invention may be implemented.

Referring to FIG. 1 of the drawings, an example of a diamond mine processing system is generally indicated by reference numeral 12. Diamond detection will be used as an example implementation of embodiments of the invention in this description. However, it should be appreciated, especially by those skilled in the art that alternative embodiments extend to other types of detection and to imaging applications in high volume and high rate environments, e.g. PET imaging/detection applied to the body of a human or animal (such as total-body medical PET and PET video).

The system 12 typically includes a classification or detection system 10 which is usually a computerised system configured to perform imaging and to detect diamonds as individual, separate objects, as embedded in host objects or as objects included in a mass of other objects.

The diamond mine processing system 12 may be located at or adjacent a diamond mine and may comprise suitable conventional mining equipment such as a crusher 14 to coarsely crush mined rock to sizes of approximately 160 mm diameter, or less. The system 12 further comprises a suitable irradiator 16 to irradiate the crushed rock with photons. The photons which irradiate the rock may be from gamma ray beams from bremsstrahlung of approximately 40 MeV electrons. Instead, or in addition, these photons may be from inverse Compton scattering, plasma wakefield device, or the like. The photons are at an energy at which giant dipole resonance (GDR) occurs due to a nuclear reaction between the photons and carbon in the rock.

The system 12 comprises a hopper arrangement 18, 19 to hold the irradiated rock for a predetermined period of time. The irradiated rock returns to moderate levels of specific activity within minutes, by which time PET isotopes represent the dominant residual activity. In this regard, the hopper arrangement 18, 19 is configured to hold the irradiated rock for a hold-time of between twenty and thirty minutes at which time the $^{11}C$ PET isotope is the dominant activity. The hopper arrangement 18, 19 may then automatically release the rock after the hold-time.

The system 12 comprises a conveyor arrangement 20 comprising suitable conveyor belts which are non-attenuating to PET photons to transport rock in the system 12 in an automated fashion. The conveyor arrangement 20 may be configured to transport rock in a rock stream at a constant predetermined speed in the system 12, for example, 1 m per second.

The system also comprises a detector arrangement 22 which is located downstream from the hopper arrangement 18, 19 and adjacent the conveyor arrangement 20, particularly the belt thereof, so as to detect PET photons emitted therefrom.

Figure 2:
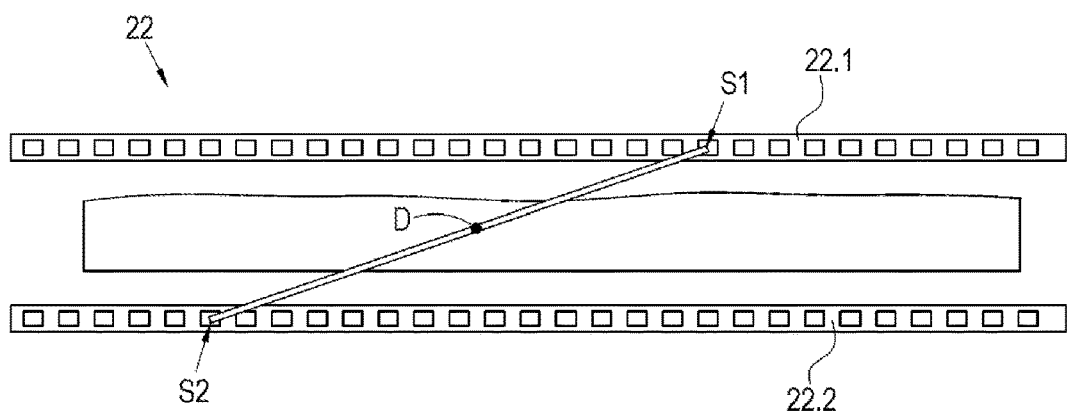
FIG. 2 shows an illustration of kimberlite rock on a moving belt between detector planes of a detector arrangement in accordance with an example embodiment of the invention, showing two coincident back-to-back 511 keV gamma rays, which together form a line of response (LoR)

In one example embodiment, and as shown in FIGS. 1 and 2, the detector arrangement 22 may comprise a pair of detector arrays 22.1 and 22.2 which are located above and below the belt, respectively, so as to be seen to effectively sandwich the belt and rock travelling thereon. In other embodiments the detector arrangement may be configured differently, e.g. it may be substantially cylindrical such that it completely circumscribes the belt.

The array 22.1 may define a top detector plane which consists of a plurality of individual detectors or detector units and the array 22.2 may define a bottom detector plane which consists of a plurality of individual detectors or detector units. The arrays 22.1, 22.2 have sensing axes which are substantially transverse to a direction of travel A of the rock. In one example embodiment, the detector arrangement 22 comprises detectors suitable for detecting photons. In this regard the detectors of the arrangement 22 may be in the form of scintillator crystals and photomultiplier tube (PMT) detectors with suitable electronics.

The system 12 also comprises a suitable sorter 24 which may be an electronically controlled mechanical sorter 24 configured to sort potentially diamondiferous or in other words diamond containing rocks or loose diamonds from potentially barren rocks or in other words rocks without diamonds therein.

The detection system 10 is communicatively coupled to the detector arrangement 22 and to the sorter 24 so as to receive classification data from the detector arrangement 22 and to generate suitable control signals to control the sorter 24 to sort diamondiferous rocks from barren rocks. In this regard, it is important for the system 10 to process the classification data with sufficient speed in order to be able to send the activation signal (data) to the sorter 24 in time. The system 10 may include various computing components, such as those referred to with reference to FIGS. 5 to 10 below.

The sorter 24 may be configured to sort diamonds or diamondiferous rocks into one or more categories according to one or more specific properties of the diamond/diamondiferous rock detected, as opposed to simply sorting the same from barren rocks.

The system 10 may be coupled to the detector arrangement 22 and/or the sorter 24 in a hardwired fashion, or in a wireless fashion. In one example embodiment, the system 10 is communicatively coupled to the arrangement 22 via a communications network which may comprise one or more different types of communication networks. In this regard, the communication network may be one or more of the Internet, a local area network (LAN), a wide area network (WAN), a metropolitan area network (MAN), various types of telephone networks (e.g., Public Switch Telephone Networks (PSTN) with Digital Subscriber Line (DSL) technology) or mobile networks (e.g., Global System Mobile (GSM) communication, General Packet Radio Service (GPRS), Code Division Multiple Access (CDMA), and other suitable mobile telecommunication network technologies), or any combination thereof. It therefore follows that though it may not necessarily be practical, it is envisaged that in some example embodiments, the system 10 need not be at the site of the mine but may be remote therefrom. In some embodiments, the arrangement 22 may form part of the system 10.

The system 10 is configured/programmed to receive classification data and to determine whether or not the object is potentially a diamond or diamondiferous by processing the received classification data. The classification data is typically associated with photons detected by the arrangement 22 which are emitted from the object as a result of positron annihilation in the irradiated object received from the hopper 18. In particular, referring to FIG. 2 of the drawings, when a PET isotope in the kimberlite rock releases a positron particle through beta-decay, the positron annihilates with a nearby electron after following a short path that can involve multiple scattering events. The most common outcome of this annihilation is the production of nearly co-linear back-to-back 511 keV gamma ray photons. Each photon then travels through the surrounding material, sometimes changing energy and direction along the way. When the photons reach the detector arrangement arrays 22.1, 22.2 at S1, S2, the arrangement 22 outputs classification data in the form of detector strike/hit event data, for example, which comprises data indicative of the location of the hit on the arrays 22.1, 22.2, the energy of the photon, and a time stamp. This allows the position of a diamond (see "D" in FIG. 2) to be determined or estimated.

As explained above in the "Background" section above, the elementary unit of a PET image is the line of response (LoR), resulting from position sensitive detection of a single positron annihilation event by the detector arrangement 22. In this regard, approximately a million such events may be required per rock (10 cm diameter) in order to detect diamonds therein. The LoR must be processed into PET reconstructed images in 3D with voxel sizes of millimetric dimensions. It follows that hundreds of these images must be analysed per second in a typical 700 tons per hour throughput. Thus, the detection system 10 and/or the detector arrangement 22 may have significant processing, transmitting and/or computational burdens.

Embodiments of the present invention deal with the management of high throughput data in a detection system such as the system 10. The data transmitted and/or processed by such a system may exceed the transport capacity of a single high bandwidth link or the processing capacity of a single computer.

A principle that may be employed to manage high throughput data is so-called "parallelisation". This means that a data set must be segmented into separate streams which each have a sufficiently low throughput rate that they can be accommodated both within the bandwidth of the communication links and the processing power of the computers in the detection system in a sufficiently short time. Parallelisation does not refer to a simple segmentation of data flow. The segments must relate to regions of interest (RoI), which must be carefully chosen, as will be illustrated below. Preferably, the RoIs should have a low correlation between each other, so that all the data for a given RoI is sufficient for processing of that RoI.

Furthermore, several levels of parallelisation may be defined. One relates to segmenting a detection system or detector arrangement into detector RoIs, another relates to segmenting a rock stream into moving rock collection RoIs. A third segmentation level relates to segmenting a computer analysis system as necessary to accomplish the required analysis in a sufficiently short time. Examples of these levels of parallelisation are presented below.

Figure 3:
FIG. 3 shows a conceptual side view of a detector arrangement in which adjacent detectors in opposite planes are linked, according to an embodiment of the invention.
Figure 4:
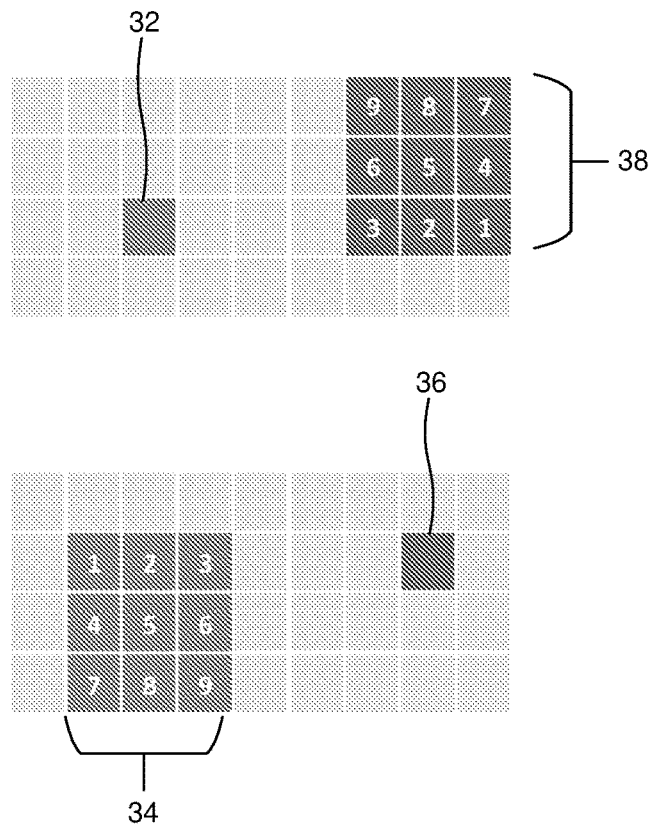
FIG. 4 conceptually shows the joining of detectors in top and bottom detector planes of the detector arrangement of FIG. 3.

A first parallelisation example is illustrated in FIGS. 3 and 4 and relates to the partitioning of coincidence triggering.

The detector arrangement 26 of FIGS. 3 and 4 includes a top detector array (hereinafter "the top plane 28") and a bottom detector array (hereinafter "the bottom plane 30").

Partitioning is performed by the detection system which can recognise specific links or associations between individual detectors in the top plane 28 and bottom plane 30. The trigger unit is configured to receive detection signals (fast signals) from the individual detectors of the detector arrangement 26. Fast signal lines representing clocked singles detections (of appropriate parameters) from a detector to the external coincidence unit may all be length-matched so that there is no time delay differential in the signals from different detectors as they are transported to the external coincidence unit.

If the arrival times of the fast signals received from two detectors are within the coincidence window, the external coincidence trigger unit sends trigger information indicative of a coincidence signal (fast strobe signal) back to both detectors in question (i.e. one in the top plane 26 and one in the bottom plane 28) and they can then transmit, report or publish their events to a network or detection system. These events may be buffered to de-randomise the event rate, allowing a higher data throughput rate. If a detector does not receive trigger information indicative of a coincidence confirmation strobe signal from the external trigger unit, the event is aborted without requiring any further processing and lengthy event building, and the detector is free to detect the next event. This minimises detector busy time.

Partitioning of the raw detector output over topologically separate networks, for the purpose of handling a high raw data rate is based on the geometrical position of the LoR and the increasing decorrelation of LoRs that relate to source points that are further away from each other. Partitioning is therefore geometry based. A LoR arises from a valid coincidence recorded in two different places of the detector. The term valid relates to the time window of the coincidence and also to the spatial relationship of the LoR endpoints. There are several methods by which the valid condition can be implemented, and also it can be implemented at different levels of the paralellisation. As one example, the detector unit that has been triggered as having detected at least one of two coincident LoR endpoints, publishes this endpoint information to one or more separate systems at the next (DAQ) level. It will publish to more than one DAQ level system if there is ambiguity as to which detector RoI could have received the partner endpoint of the LoR. The geometrical part of the criteria for the validity of the LoR will then be determined at the DAQ level, and the LoR can be correctly formed. Also at this stage the assignment of the LoR to a virtual basket of moving rock can be established, for correct onward transmission There can also be a separate fast system at the detector level of parallelisation that establishes if the LoR endpoints would have the correct spatial relationship. Conceptually this is always possible as there is the capacity for adding sufficient intelligence within the local detection system, to establish if the endpoints of the LoR fall within a condition of the correct spatial relationship.

In the example of FIGS. 3 and 4, detectors in the detector arrangement 26 are partitioned by a method as just discussed above. This allows only coincidences or associations/links between detectors that are close to each other, based on geometrical considerations. For example, a given detector 32 of the top plane 28 is joined to 9 detector units (marked 1 to 9 and labelled "34" in FIG. 4) beneath it from the bottom plane 30: one directly below, four directly adjacent, and four diagonally adjacent, as shown in FIG. 4. Similarly, a detector 36 of the bottom plane 30 may be jointed to 9 detector units (marked 1 to 9 and labelled "38" in FIG. 4) in the top plane 28. FIG. 3 illustrates lines depicting adjacent detectors in opposite planes 28, 30 that can form coincidences. Each of these sets of "joined" detectors may be said to form a separate RoI, which consists of a subset of the total number of detectors used.

By restricting the number of detectors that can form coincidences or matches, it is possible to have a large detection system (e.g. one with higher activation, higher throughput, higher capacity and/or higher speed) with substantially the same false positive rate as a significantly smaller detection system. The partitioning described with reference to FIGS. 3 and 4 does not allow oblique LoRs. In this regard, it will be noted that oblique LoRs have to travel on average through a lot of rock, which means that one or both 511 keV photons are very likely to be absorbed or scattered along the way. Oblique LoRs are therefore rare as they are suppressed due to geometrical considerations o the rock. On the other hand, in a large detector array, false positive oblique LoRs are relatively more common, because if one picks a random event from the top plane and a random event from the bottom plane, which happen to arrive within the coincidence window, the chances are that they will not be directly above each other. Altogether, this means that if one sees an oblique LoR, it is likely that is not a true LoR, but rather a random coincidence of unrelated events in different parts of the detector. Finally, when one does get true oblique coincidences, they are more likely to be inaccurate, because of the high scattering probability. In view of the foregoing, cutting out oblique LoRs in the context of the example embodiment under discussion is desirable.

Notwithstanding, it will be appreciated that in some example embodiments of the invention, oblique LoRs may be valuable in detector arrangements where there is a detector plane above and below the rock, but no detectors on the side. This lack of information from side angles means that the detector's resolution suffers in the Z direction, and point sources end up looking like cigars, spread out from top to bottom. Oblique LoRs give information from underrepresented side angles. Past approximately 45 degrees, the advantages of cutting out oblique LoRs may outweigh the advantages of including them. It will be appreciated by those skilled in the field of invention that there may be MinPET detector geometries that do indeed have a full overage of all angles (sides) of the LoRs.

Figure 5:
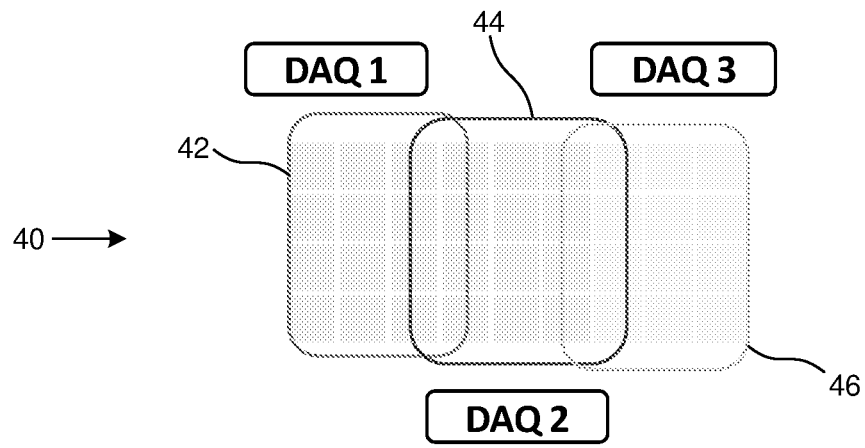
FIG. 5 conceptually shows a first example of the association of detectors with data acquisition (DAQ) computers, according to an embodiment of the invention.
Figure 6:
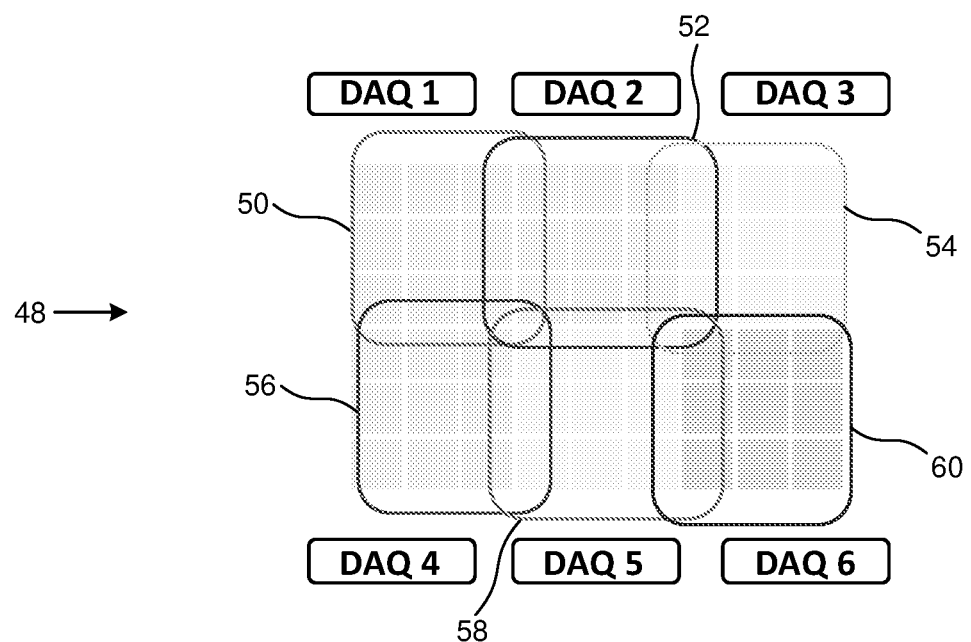
FIG. 6 conceptually shows a second example of the association of detectors with DAQ computers, according to an embodiment of the invention.

A second parallelisation example is illustrated in FIGS. 5 and 6 and relates to the partitioning of LoR formation.

It will be understood that each detector only has access to "its own" information, i.e. information about a single event from one side of an array of detectors, together with information included in a signal from an external coincidence trigger unit. Forming LoRs therefore relies upon considering a list of single events from the opposing detector planes, e.g. top and bottom planes 28, 30 as described with reference to FIGS. 3 and 4, and matching these events into their correct pairs to form LoRs based on the coincidence window and a high time resolution time stamp associated with the event.

If each detector in a large detection system publishes each event to the same processing receiving computer, this may saturate the data transfer capabilities of the network and the processing capabilities of a single machine to perform event matching. Embodiments of the invention therefore provide for the parallelisation of LoR formation over several data acquisition (DAQ) computers, each configured to do processing separately. This partitioning takes advantage of the knowledge of the geometrical source point of the end of a candidate LoR. The local detector unit responsible for this hit detection will only publish its data to one or more DAQ computers, over a specific network, based on the possible RoIs this candidate LoR endpoint may belong to. The DAQ computer which also receives the other end of the candidate LoR, can test for a temporal and geometrical match. It can the build the LoR and determine to which virtual basket moving on the belt it belongs to and send it for onward processing, also over a specific independent topological network to in the parallelised system. One may also have a supervisory hardware/firmware/software layer that is able to determine at trigger level the RoI of the LoR to perform the same function described above more efficiently. external coincidence trigger unit technique discussed above. This restricts coincidences to adjacent detectors or detectors identified to belong in the same RoI, it may be impossible for detectors from relatively distant sections of the system to form LoRs. Each DAQ computer may therefore only receive events from detectors that are close to each other, i.e. as being very likely to be in the same RoI.

Examples of the partitioning of detectors to DAQ computers are shown in FIGS. 5 and 6. In the context of this specification, the term "computer" in "DAQ computer" should be broadly interpreted and may refer to one or more processor, one or more computer system, a server, a cluster of computers, or the like.

FIG. 5 illustrates a detector plane 40, i.e. a detector array, which has been divided into three RoIs 42, 44, 46. Each RoI 42, 44, 46 includes a 3×4 set of individual detector units and is associated with a particular DAQ computer (labelled DAQ1, DAQ2 and DAQ3 in FIG. 5). It will be understood that each 3×4 set may be paired with a corresponding 3×4 set, e.g. above or below it or otherwise locating in an opposing plane, to form the entire RoI in question.

FIG. 6 illustrates another example of a detector plane 48. The plane 48 is divided into six RoIs 50, 52, 54, 56, 58, 60. Each RoI 50, 52, 54, 56, 58, 60 includes a 3×3 set of detector units and is associated with a particular DAQ (labelled DAQ1, DAQ2, DAQ3, DAQ4, DAQ5 and DAQ6 in FIG. 6).

The RoIs in FIGS. 5 and 6 are shown as overlapping, because the trigger unit may in some embodiments allow coincidences between adjacent detectors. In the worst-case scenario, therefore, detectors on the corners of overlapping regions would need to send each event to four different DAQ computers, as the LoR could be in one of four overlapping DAQ areas of responsibility.

Figure 7:
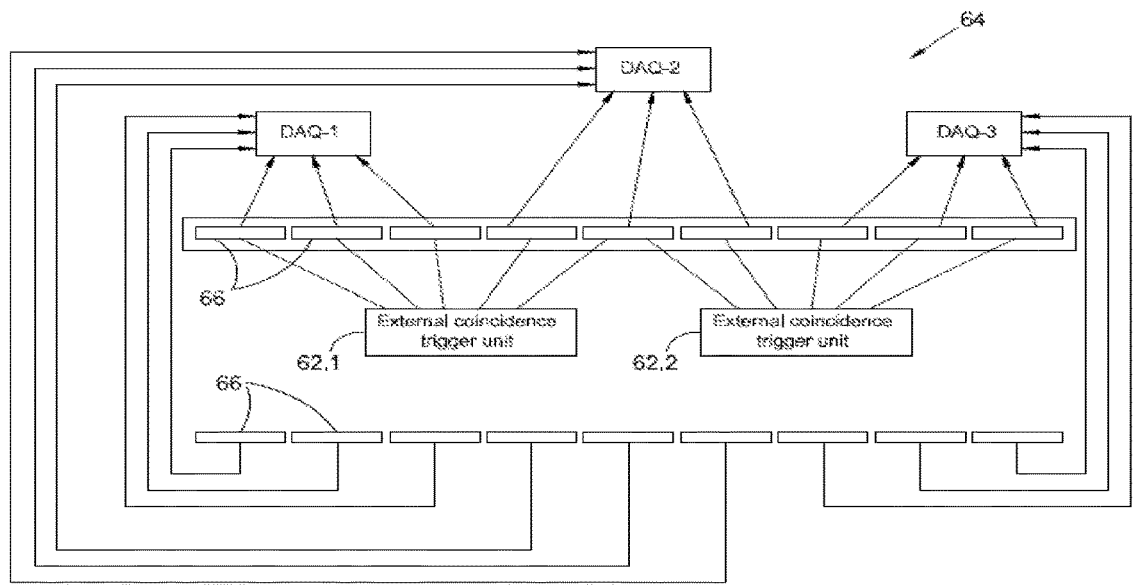
FIG. 7 shows a first example of a network topology which includes connections between detectors and external coincidence trigger units, as well as between the detectors and DAQ computers, according to an embodiment of the invention.

Each detector in detection systems according to embodiments of the invention may have two connections. One may be a bi-directional connection to coincidence trigger units 62.1, 62.2. The example topology 64 of FIG. 7 shows these bi-directional connections as broken lines. These connections may handle signals from different detectors 66 in parallel, so that total data transfer rate does not become problematic. The other type of connection may be a unidirectional connection via which the detectors 66 send event data to DAQ computers, shown as solid arrows in FIG. 7.

It will be understood that one, or a plurality of coincidence trigger units may be included in detection systems in embodiments of the invention. In some cases, internal coincidence trigger unit/s (i.e. forming part of a detector arrangement), providing the same functionality as the external coincidence trigger unit/s described herein, may be employed.

The DAQ computers associated to each RoI may be responsible for examining events and combining pairs of single hit events (which are known to have coincident partners) into LoR events for that RoI, and each such DAQ computer may be in the form of a physically and/or logically separate topological network, system or arrangement to reduce the data rate of the overall detection system into sub-rates on separate networks, systems or arrangements.

Figure 8:
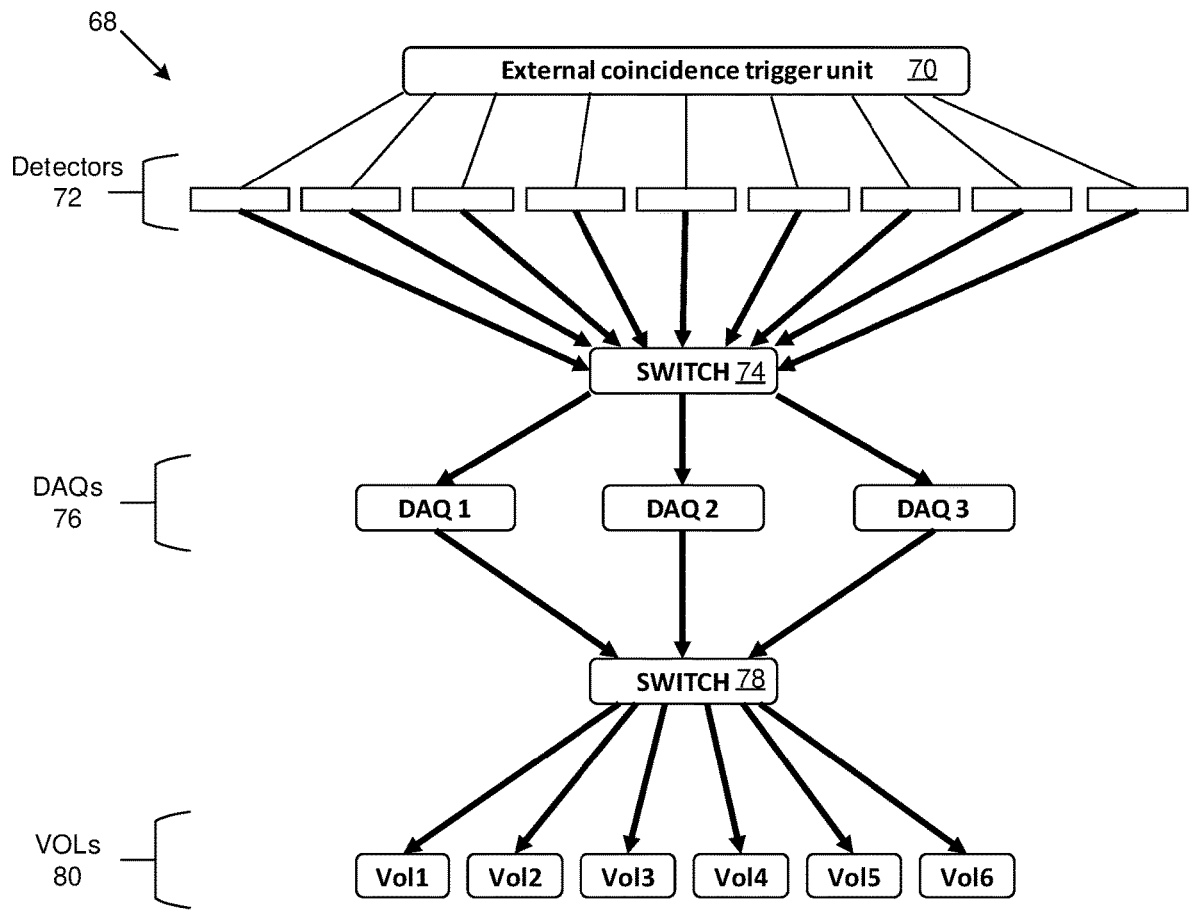
FIG. 8 shows a second example of a network topology which includes various levels of detection system partitioning, according to an embodiment of the invention.
Figure 9:
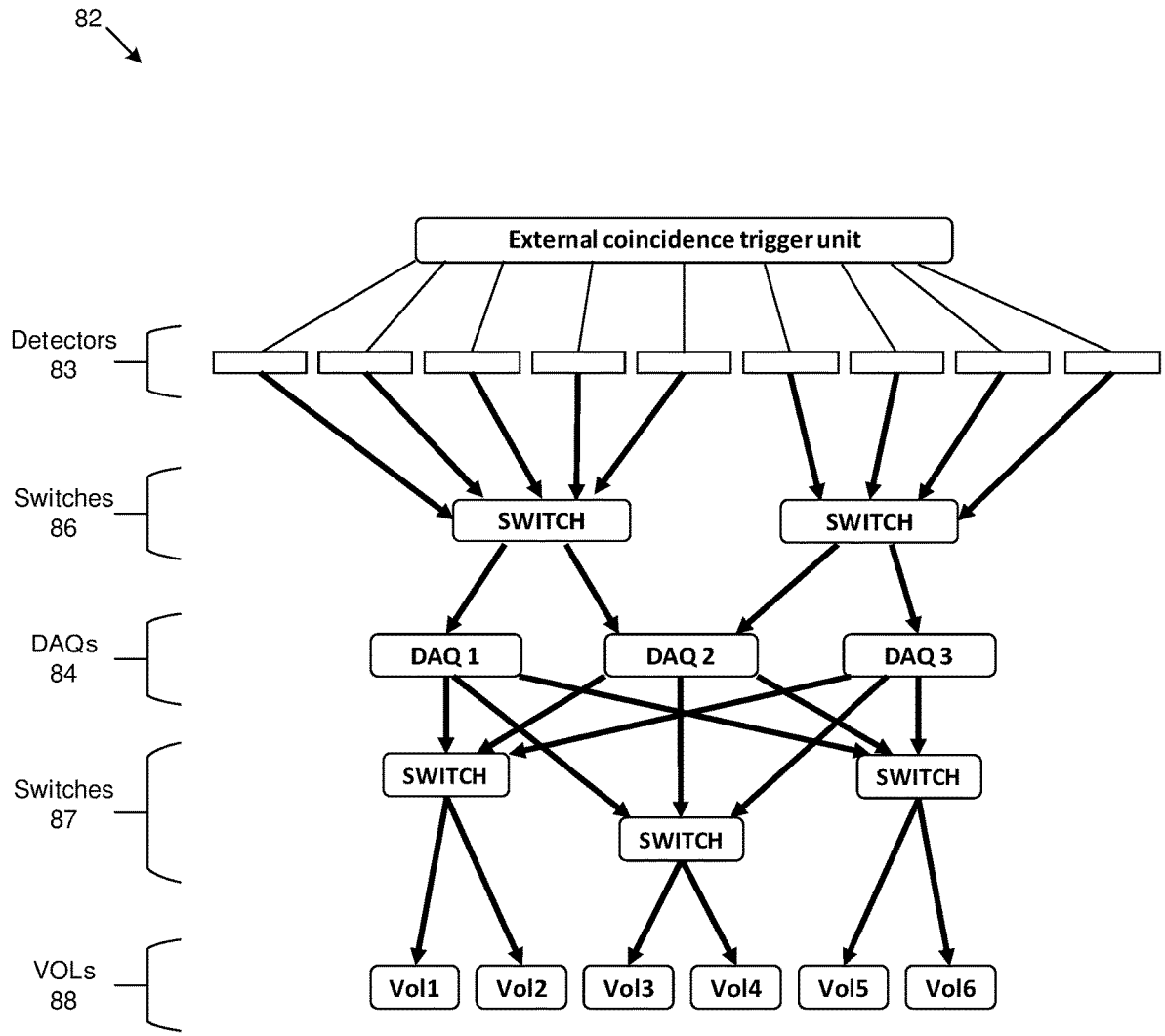
FIG. 9 shows a third example of a network topology which includes various levels of detection system partitioning, according to an embodiment of the invention.

A third parallelisation example is illustrated in FIGS. 8 and 9 and it relates to partitioning into so-called "moving volumes".

In many cases, no single processing node will be able to complete PET reconstruction and diamond detection in real time for a reasonably sized detection operation. Some embodiments of the invention thus allow for the parallelisation of volumes and processing nodes. As explained with reference to the example in FIG. 1, each rock particle may move through a detector system along a conveyor belt. PET reconstruction may be parallelised into volumes that are fixed to belt position, as opposed to LoR formation, where fixing is with respect to detector positions. The RoIs for rocks moving on a stream may be thought of as co-moving and also in some cases overlapping "virtual rock containers".

Time stamp information and end point positions of each LoR may be used to calculate which belt-fixed volume(s) it intersects. The rock stream on the belt may be pre-divided into the overlapping virtual containers. The LoR is then associated with at least one particular co-moving virtual container. The package of LoRs for that virtual container are transmitted to a node, computer, processor or computing system known as a "VOL", as it is specific to particular virtual container (volume) of rock. The subset of the LoRs within each volume (virtual container) may then be processed by its own "VOL" to from a PET image, and this PET image may be analysed to determine whether a diamond is present. PET images from various "VOLs" may also be combined into a larger image if required.

This processing may be farmed out by further segmentation as required, in the interests of factors such as speed.

An embodiment of a network topology 68 enabling various levels of partitioning, including dividing the system into moving volumes, is shown in FIG. 8. In this arrangement, detectors 72 communicate with a coincidence trigger unit 70 in the manner described above. The detectors 72 send event data to DAQs 76, each of which is responsible for a sub-volume of the overall detection system. The DAQs 76 send LoRs to belt-fixed volume processors 80. In one embodiment, each belt-fixed volume is handled by a single processing node (e.g. there may be a total of six virtual containers, as shown and labelled Vol1 to Vol6 in FIG. 8). The node accumulates LoRs while the volume it is associated with is analysed by the detectors 72. As soon as the volume leaves the detectors 72, the node proceeds to PET reconstruction, and analysing for diamonds. After that, the node can be recycled, and assigned a new volume at the start of the detector system.

If data transfer capabilities of the network's switches 74, 78 are a bottle-neck, more complex network topologies may be constructed to allow data transfer in parallel. For example, in the topology 82 shown in FIG. 9, a possible bottleneck between the detectors 83 and the DAQ computers 84 is removed by grouping the detectors 83 into sub-networks with different switches 86. These switches are in turn each connected to the DAQ computers 84 that handle coincidence formation from the detectors 83 that are within each sub-network. If sub-networks are formed from detectors that are close together, then each sub-network may only need to be connected to a subset of the DAQ computers 84.

Furthermore, a possible bottleneck between the DAQ computers 84 and the belt-fixed volume processors 88 may be removed by assigning sets of volumes to different switches 87. Each DAQ computer 84 may be connected to each of the switches 87, as shown the example of FIG. 9.

Figure 10:
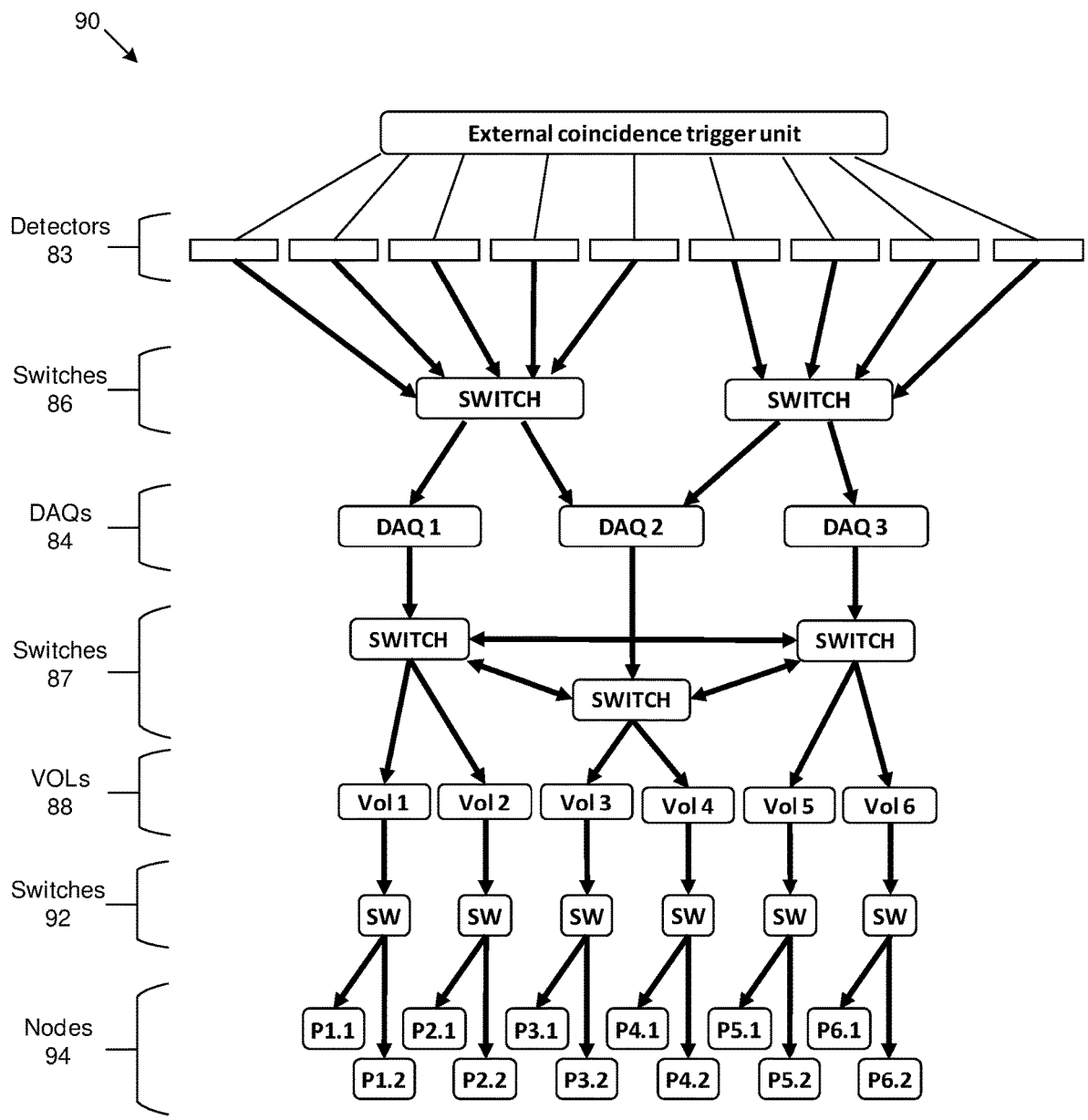
FIG. 10 shows a fourth example of a network topology which includes various levels of detection system partitioning, according to an embodiment of the invention.

A fourth parallelisation example is illustrated in FIG. 10 and it relates to further partitioning of processing nodes associated with belt-fixed volumes. The topology 90 of FIG. 10 is similar to that of FIG. 9 and like reference numerals refer to like components.

It may prove advantageous to further partition each belt-fixed volume into several processing nodes 94 via further switches 92. This allows each processing node 94 to handle a relatively small sub-volume of a "virtual container", to aid in image reconstruction, while the belt-fixed volumes can remain larger. This may have at least two benefits: firstly, there are not too many volumes present on the network. Secondly, duplication of LoRs may be reduced. Duplication may arise when the belt-fixed volumes become smaller, because each LoR could potentially pass through several volumes.

As shown in FIG. 10, each VOL 88 may be provided with a further layer of processing nodes (e.g. nodes P1.1 and P1.2. which serve Vol1 via one of the switches 92). The topology 90 of FIG. 10 further differs from the topology 82 of FIG. 10 in that, in the topology 82, each DAQ 84 is connected to all the switches 87, while in the topology 90 each DAQ 84 is connected to one switch 87 with interconnections being provided between the switches 87 themselves. The reason for this is that the arrangement of FIG. 9 may not be scalable beyond a certain point. It may thus be necessary to add a layer of interconnection between the switches 87. While this may add a step to the route followed by each LoR, it is likely to be more scalable in terms of the number of switches between DAQ computers and belt-fixed volumes.

The topologies 64, 68, 82, 90, or parts thereof, may form part of a detection system for use in diamond detection, e.g. the detection system 10 of FIG. 1.

Figure 11:
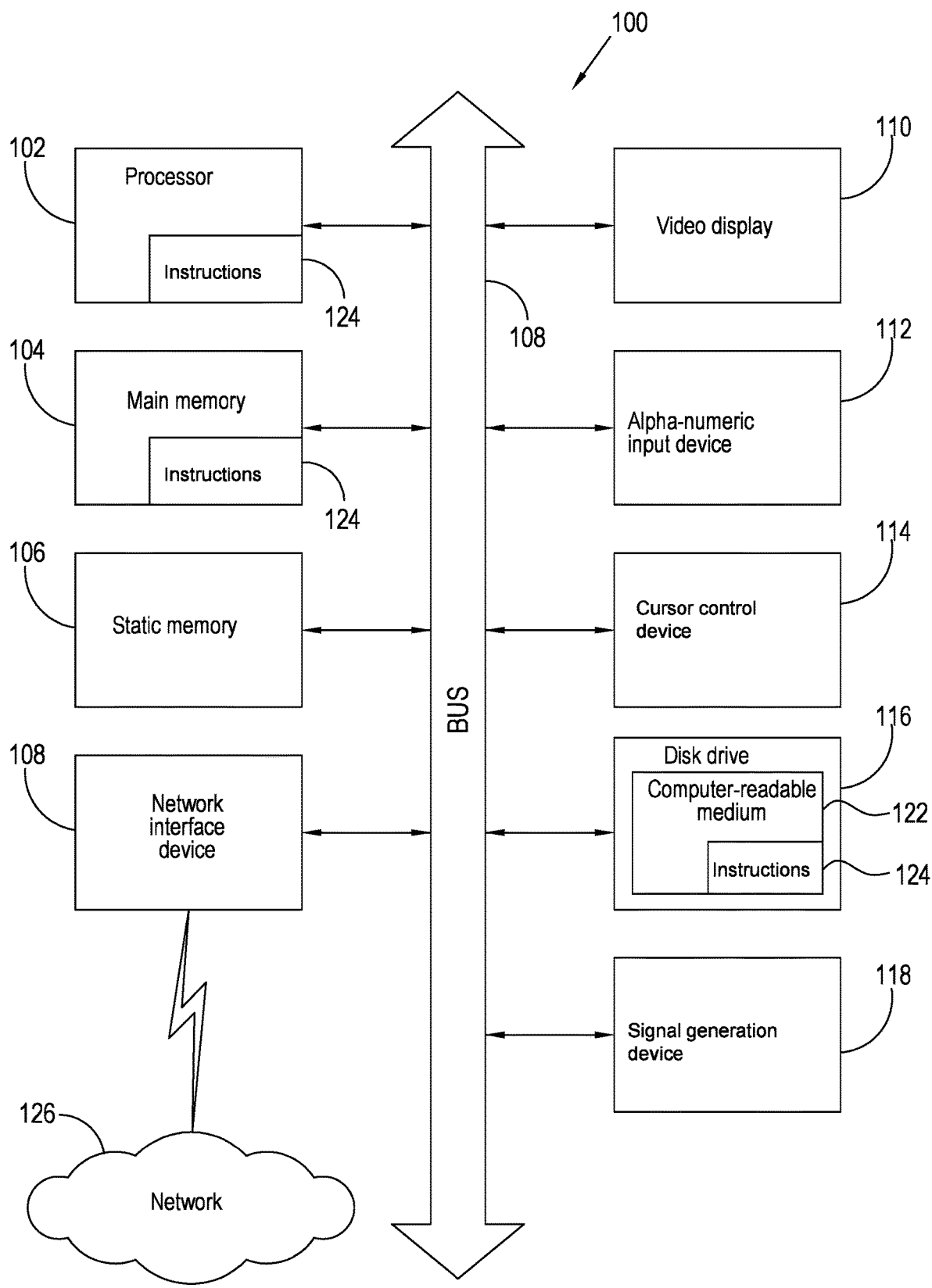
FIG. 11 shows a diagrammatic representation of a machine in the example form of a computer system in which a set of instructions for causing the machine to perform any one or more of the methodologies discussed herein, may be executed.

Referring now to FIG. 11 of the drawings which shows a diagrammatic representation of the machine in the example of a computer system 100 within which a set of instructions, for causing the machine to perform any one or more of the methodologies discussed herein, may be executed. In other example embodiments, the machine operates as a standalone device or may be connected (e.g., networked) to other machines. In a networked example embodiment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated for convenience, the term "machine" shall also be taken to include any collection of machines, including virtual machines, that individually or jointly execute a set (or multiple sets) of instructions to perform any one or more of the methodologies discussed herein.

In any event, the example computer system 100 includes a processor 102 (e.g., a central processing unit (CPU), a graphics processing unit (GPU) or both), a main memory 104 and a static memory 106, which communicate with each other via a bus 108. The computer system 100 may further include a video display unit 110 (e.g., a liquid crystal display (LCD) or a cathode ray tube (CRT)). The computer system 100 also includes an alphanumeric input device 112 (e.g., a keyboard), a user interface (UI) navigation device 114 (e.g., a mouse, or touchpad), a disk drive unit 116, a signal generation device 118 (e.g., a speaker) and a network interface device 120.

The disk drive unit 16 includes a non-transitory machine-readable medium 122 storing one or more sets of instructions and data structures (e.g., software 124) embodying or utilised by any one or more of the methodologies or functions described herein. The software 124 may also reside, completely or at least partially, within the main memory 104 and/or within the processor 102 during execution thereof by the computer system 100, the main memory 104 and the processor 102 also constituting machine-readable media.

The software 124 may further be transmitted or received over a network 126 via the network interface device 120 utilising any one of a number of well-known transfer protocols (e.g., HTTP).

Although the machine-readable medium 122 is shown in an example embodiment to be a single medium, the term "machine-readable medium" may refer to a single medium or multiple medium (e.g., a centralized or distributed memory store, and/or associated caches and servers) that store the one or more sets of instructions. The term "machine-readable medium" may also be taken to include any medium that is capable of storing, encoding or carrying a set of instructions for execution by the machine and that cause the machine to perform any one or more of the methodologies of the present invention, or that is capable of storing, encoding or carrying data structures utilised by or associated with such a set of instructions. The term "machine-readable medium" may accordingly be taken to include, but not be limited to, solid-state memories, optical and magnetic media, and carrier wave signals.

Embodiments described herein may provide numerous advantages. For instance, by linking detectors only to those adjacent to them, and in particular only to those above or below them or otherwise close to them in an opposing plane, data output rate may be lowered and false positives may be reduced (by controlling geometrical effects).

A detector arrangement may be divided into RoIs to ensure that only, or mostly, valid events are broadcast for processing. Parallelisation may be employed in the network topology of a detection system so that each detector can direct its output to a relevant topological network segment. It is envisaged that in some implementations data may be re-shared if it is found also to be relevant to another topological network segment. A portion of data could also be processed more than once in several segments. This overlap of detector segment data may be tolerable as the overall rate capacity per segments may still be increased.

Work to be carried out by a detection system may be physically and/or logically partitioned at different stages, in order to allow processing and data transfer to happen in parallel. As described above, partitioning can be based on detector positions (i.e. separation of coincidence triggering or separation of LoR formation), on volumes moving relative to the detector arrangement, and/or on the separation of a detection system into separate and parallel processing nodes.

Embodiments of the invention may make it possible to collect and handle more data. In turn, this may make it possible to detect relatively small diamonds and to detect diamonds in relatively large objects, such as large kimberlite particles. Furthermore, the parallelisation techniques described herein may permit a detection system to operate at an increased throughput level.

It is envisaged that at least some of the techniques and architectures described herein may find application outside of diamond (or other precious particle) detection. For instance, at least some of the techniques and architectures described herein may be applied in PET imaging/detection applied to the body or a body part of a human or animal.

The invention claimed is:

1. A detector arrangement comprising a pair of spaced apart detector arrays oriented generally parallel to each other, wherein the detectors are configured to detect photons emitted from an object, wherein each detector in one of the arrays is linked to or associated with one or more other detector in the other one of the arrays to define a region of interest (RoI), each RoI including a subset of the detectors in the pair of arrays, and wherein the detector arrangement comprises or is communicatively coupled to a coincidence trigger unit which is configured to register or determine a coincidence in response to receiving detection signals from two different detectors forming part of the same RoI and indicating detection of substantially back-to-back co-linear and co-incident photons in the RoI.

2. The detector arrangement as claimed in claim 1, wherein the detectors are configured to detect photons emitted from the object as a result of positron annihilation due to irradiation of the object with photons of a predetermined energy.

3. The detector arrangement as claimed in claim 1, wherein each RoI includes at least one detector from each detector array and the coincidence trigger unit is configured to register a coincidence in response to receiving detection signals from a detector from each detector array, provided the detectors are in the same RoI.

4. The detector arrangement as claimed in claim 1, wherein each RoI includes one detector from one of the arrays and a plurality of detectors from the other one of the arrays.

5. The detector arrangement as claimed in claim 1, wherein the coincidence trigger unit is configured, in response to registering a coincidence, to transmit a coincidence signal back to each of the two detectors as trigger information indicative thereof.

6. The detector arrangement as claimed in claim 5, wherein the detectors are configured to transmit or publish event data relating to the registered coincidence signal to a specific data acquisition (DAQ) computer in response to receiving trigger information indicative of a coincidence signal.

7. A detection system which comprises:
   a detector arrangement comprising at least one array of detectors, wherein the detectors are configured to detect photons emitted from an object, wherein each detector in the array is linked to or associated with one or more other detector in the array to define a region of interest (RoI), each RoI including a subset of the detectors in the array;
   a coincidence trigger unit forming part of or communicatively coupled to the detector arrangement, wherein the coincidence trigger unit is configured to register or determine a coincidence in response to receiving detection signals from two different detectors forming part of the same RoI and indicating detection of substantially back-to-back co-linear and co-incident photons in the RoI; and
   a plurality of data acquisition (DAQ) computers configured to receive event data from the detector arrangement, wherein the event data is related to a coincidence registered or determined by the coincidence trigger unit, wherein each DAQ computer is configured to receive event data only from detectors which form part of one or more RoIs which are associated with the particular DAQ computer.

8. The system as claimed in claim 7, wherein the photons emitted from the object are as a result of positron annihilation due to irradiation of the object with photons of a predetermined energy.

9. The system as claimed in claim 7, wherein the event data is raw output data from the detector arrangement and each DAQ computer is configured to determine a line of response (LoR) based on the raw output data received from the detector arrangement.

10. The system as claimed in claim 9, wherein the LoR corresponds to an imaginary line through the object connecting strikes on detectors on opposite sides of the object, with the strikes corresponding to the back-to-back co-linear and co-incident photons emitted by or from the object.

11. The system as claimed in claim 7, wherein the detector arrangement is configured to perform detection on a stream of objects passing through the detector arrangement, wherein the detection system is configured to divide the stream of objects into virtual containers, wherein each LoR is associated with at least one virtual container.

12. The system as claimed in claim 11, wherein each DAQ computer is configured to transmit LoRs to a volume processing computer or subsystem configured to process only LoRs relating to one or more particular virtual container, wherein the volume processing computer or subsystem is configured to form a positron emission tomography (PET) image based on LoRs associated with a particular virtual container.

13. The system as claimed in claim 11, wherein the virtual containers are fixed to belt-moving coordinates.

14. The system as claimed in claim 11, wherein the DAQ computers are fixed to detector coordinates.

15. The system as claimed in claim 11, wherein the DAQ computers are not fixed to virtual containers but process a continuous procession of virtual containers.

16. The system as claimed in claim 11, wherein the detection system comprises a plurality of processing nodes associated with each virtual container and/or each volume processing computer or subsystem, such that each processing node operatively handles a sub-volume of a volume associated with each virtual container.

17. A method of processing data from a detector arrangement, wherein the detector arrangement includes at least one array of detectors, wherein the method comprises:
    linking or associating each detector in the array with one or more other detector in the array to define a region of interest (RoI), each RoI including a subset of the detectors in the array;
    detecting, by the array of detectors, photons emitted from an object
    receiving, by a coincidence trigger unit, detection signals from at least two of the detectors;
    registering or determining a coincidence if the coincidence trigger unit receives detection signals from two different detectors forming part of the same RoI and indicating detection of substantially back-to-back co-linear and co-incident photons in the RoI;
    transmitting, by the coincidence trigger unit, trigger information indicative of a coincidence signal to each of the two detectors in response to registering or determining the coincidence; and
    transmitting or publishing, by the two detectors, event data relating to the registered coincidence to one of a plurality of data acquisition (DAQ) computers.

18. The method as claimed in claim 17, wherein the RoIs may overlap, so the subsets of detectors that form RoIs are not mutually exclusive subsets.

19. The method as claimed in claim 17, wherein a detector in the detector arrangement that has been triggered as having detected at least one of two coincident LoR endpoints, publishes this endpoint information to one or more separate systems at a next (DAQ) level.

20. The method as claimed in claim 17, wherein the detectors of the detector arrangement have intelligence that publishes their data to a different topologically independent network of DAQ computers, thereby achieving the separation of the signals over different networks.

* * * * *